US006962011B2

(12) United States Patent
Drennan

(10) Patent No.: US 6,962,011 B2
(45) Date of Patent: Nov. 8, 2005

(54) SHOE FOR A CASTED FOOT

(76) Inventor: Denis Burke Drennan, 1316 Sherman Ave., Evanston, IL (US) 60201

( * ) Notice: Subject to any disclaimer, the term of this patent is extended or adjusted under 35 U.S.C. 154(b) by 0 days.

(21) Appl. No.: 10/711,397

(22) Filed: Sep. 16, 2004

(65) Prior Publication Data

US 2005/0060915 A1    Mar. 24, 2005

Related U.S. Application Data

(60) Provisional application No. 60/481,411, filed on Sep. 24, 2003.

(51) Int. Cl.[7] .......................... A43B 3/24; A43B 13/20
(52) U.S. Cl. ........................................... 36/110; 36/29
(58) Field of Search .............................. 36/110, 28, 29, 36/25 R, 59 R, 59 C

(56) References Cited

U.S. PATENT DOCUMENTS

| | | | | |
|---|---|---|---|---|
| 2,981,011 A | * | 4/1961 | Lombardo | 36/59 R |
| 4,020,569 A | * | 5/1977 | Fukuoka | 36/29 |
| 4,133,118 A | * | 1/1979 | Khalsa et al. | 36/83 |
| 4,178,703 A | | 12/1979 | Pols | 36/110 |
| D262,580 S | | 1/1982 | Munschy | D2/264 |
| 4,449,307 A | * | 5/1984 | Stubblefield | 36/32 R |
| 4,567,678 A | | 2/1986 | Morgan et al. | 36/110 |
| 4,599,811 A | | 7/1986 | Rousseau | 36/105 |
| 4,677,767 A | | 7/1987 | Darby | 36/102 |
| D299,787 S | | 2/1989 | Bates | D2/319 |
| 4,899,468 A | | 2/1990 | Richbourg et al. | 36/110 |
| 5,088,481 A | | 2/1992 | Darby | 602/23 |
| 5,138,777 A | | 8/1992 | Darby | 36/88 |
| D346,271 S | | 4/1994 | McDonald | D2/969 |
| D352,784 S | | 11/1994 | Cohen et al. | D24/192 |
| 5,452,527 A | | 9/1995 | Gaylord | 36/110 |
| 5,491,909 A | | 2/1996 | Darby | 36/28 |
| 5,537,764 A | * | 7/1996 | Prahl | 36/110 |
| D376,429 S | | 12/1996 | Antar | D24/192 |
| 5,839,208 A | * | 11/1998 | Huang | 36/28 |
| 5,918,385 A | * | 7/1999 | Sessa | 36/59 C |
| 5,940,992 A | | 8/1999 | Darby | 36/110 |
| D438,972 S | | 3/2001 | Darby | D24/190 |
| 6,212,798 B1 | | 4/2001 | Koenig, et al. | 36/110 |
| 6,282,818 B1 | * | 9/2001 | Lu | 36/110 |
| D454,640 S | | 3/2002 | Darby | D24/192 |
| 6,474,005 B2 | * | 11/2002 | Kobayashi | 36/127 |
| 2002/0178621 A1 | | 12/2002 | Darby | 36/140 |

\* cited by examiner

*Primary Examiner*—M. D. Patterson
(74) *Attorney, Agent, or Firm*—Gary M. Hartman; Domenica N. S. Hartman; Hartman & Hartman

(57) ABSTRACT

A cast shoe sized and configured to be worn on a casted foot. The shoe includes an air-insufflated outer sole formed of a resilient polymeric material to absorb impact. The outer sole has a heel portion of substantially uniform thickness, a tapered toe portion that is thinner than the heel portion, an upper surface, and a lower surface that has a tread pattern and is curved as a result of the tapered toe portion to provide a single rocker bottom function in gait. An inner sole overlies and is attached to the upper surface of the outer sole. A strap located adjacent the heel portion of the outer sole is provided for securing the cast shoe to a casted foot. The outer and inner soles lack any rigid member that would stiffen the sole.

20 Claims, 4 Drawing Sheets

SHOE FOR A CASTED FOOT

CROSS REFERENCE TO RELATED APPLICATION

This application claims the benefitr of U.S. Provisional Application Ser. No. 60/481,411, filed Sep. 24, 2003.

BACKGROUND OF THE INVENTION

The present invention generally relates to a shoe of a type to be worn on a casted foot, wherein the shoe is configured to cushion and protect a patient and a cast worn by the patient and to improve the gait pattern of the patient.

Shoes developed to be worn over a casted foot ("cast shoes") typically comprise a solid rigid sole formed of wood, plastic or layered material and cut in the general form of a foot. The rigid sole may be attached to an upper portion formed of a cloth, plastic, or canvas material. The upper portion is adapted to extend up both sides of the casted foot to both secure the rigid sole to the casted foot as well as provide protective coverage of the cast. The upper portion is often secured to the casted foot with a hook-and-loop closure (e.g., Velcro) or a zipper over the dorsum of the foot. The upper portion may enclose the entire foot including the toes, or leave the toes exposed. Most cast shoes marketed today have a very shallow rocker bottom sole, while others are flat. Most cast shoes also have a relatively smooth bottom surface that provides little traction.

In view of the above, there are major disadvantages with existing cast shoes. The soles of most cast shoes are too thin to offer a meaningful rocker bottom, which is necessary to improve the gait pattern of a patient wearing a cast. The soles of most cast shoes are also too rigid and solid to flex during the toe-off portion of gait or absorb any impact pressure during the heel-strike portion of gait, leading to a cast wear breakdown rate of about 40%. Furthermore, the flat smooth bottom of most current cast shoes can become slippery and unstable when wet or on slippery surfaces. Finally, hook-and-loop straps are often only loosely attached by patients or stretch out so that the shoe hangs down in the swing-through portion of the wearer's gait, causing the wearer to have a poor abduction gait pattern.

Various cast shoes have been proposed, some of which are intended to address one or more the above concerns. Examples are U.S. Design Pat. No. Des. 299,787 and U.S. Pat. Nos. 4,178,703, 4,899,468, 5,088,481, and 5,452,527. However, none satisfactorily solve each of the above-identified problems associated with cast shoes.

BRIEF SUMMARY OF THE INVENTION

The present invention provides a cast shoe, which as used herein is defined as a shoe that is specifically sized and configured to be worn on a casted foot. The shoe includes an air-insufflated outer sole formed of a resilient polymeric material to absorb impact. The outer sole has a heel portion of substantially uniform thickness, a tapered toe portion that is thinner than the heel portion, an upper surface, and a lower surface that has a tread pattern and is curved as a result of the tapered toe portion to provide a single rocker bottom function in gait. An inner sole overlies and is attached to the upper surface of the outer sole. A strap located adjacent the heel portion of the outer sole is provided for securing the cast shoe to a casted foot. According to a key aspect of the invention, the outer and inner soles lack any rigid member that would stiffen the sole so that the entire sole is flexible, particularly in the heel and toe portions during the heel-strike and toe-off portions of gait.

The cast shoe of this invention has several notable differences and advantages over the prior art that are attributable to the thickness and curvature of its outer sole, which in combination with its resilient construction promotes a truer rocker bottom function in gait. In contrast to cast shoes equipped with firm, rigid outer soles, the soft, resilient outer sole of this invention is able to absorb considerably more impact force in the weight-bearing stance phase of weight-bearing gait, particularly during the heel-strike and toe-off portions of gait. As such, the cast shoe of this invention is able to diminish patient discomfort and prolong the function of the cast and the shoe itself.

Other objects and advantages of this invention will be better appreciated from the following detailed description.

DESCRIPTION OF THE INVENTION

Figure 1:
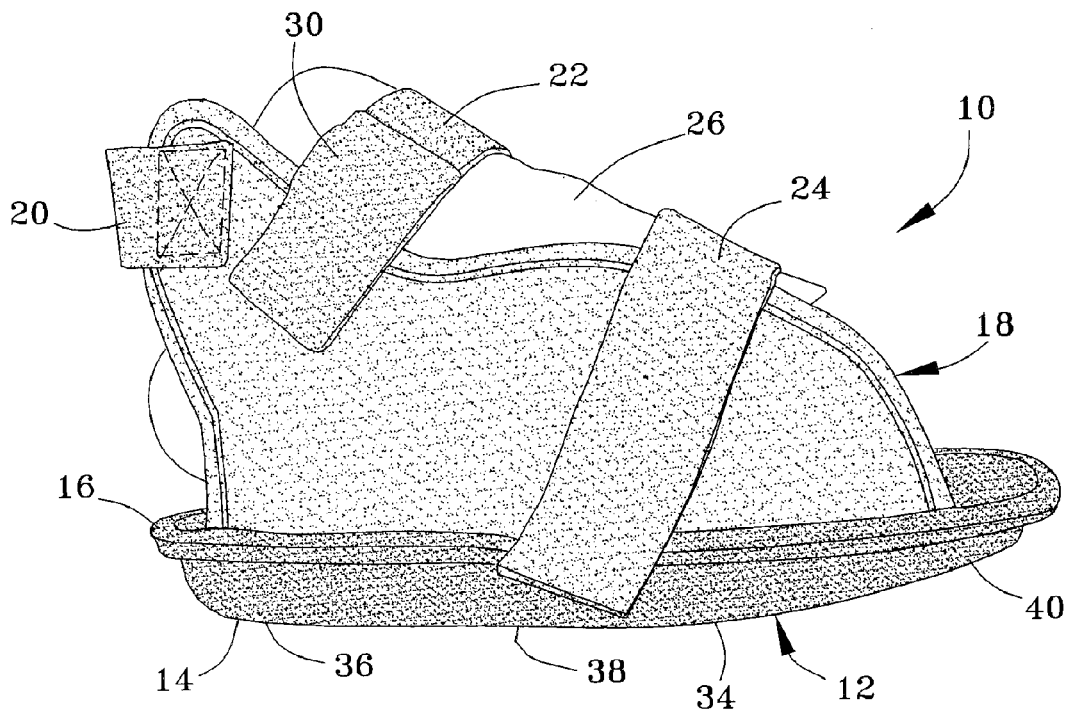
FIG. 1 is a side view of a cast shoe worn on a casted foot in accordance with an embodiment of the present invention.
Figure 2:
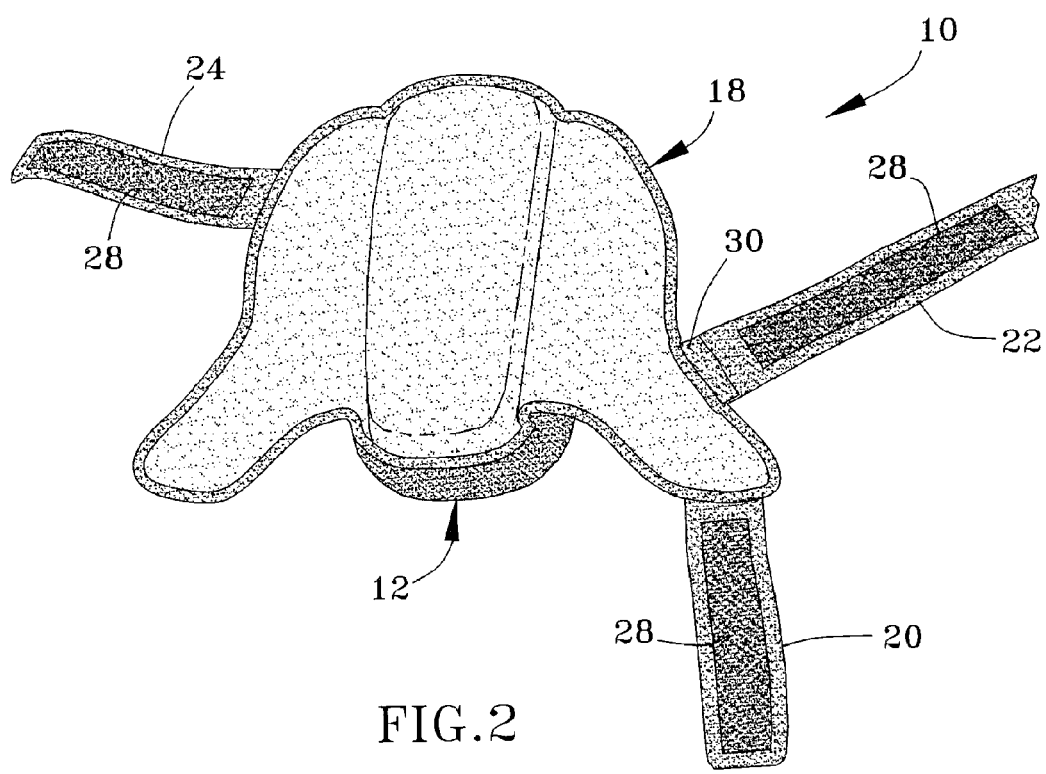
FIGS. 2 and 3 are top and bottom views of the cast shoe of FIG. 1.

FIGS. 1 through 6 show a cast shoe 10 in accordance with an embodiment of the invention. The shoe 10 can be seen to have an upper portion 18 attached to a sole 12 that comprises outer and inner soles 14 and 16. A suitable material for the upper portion 18 is canvas, though other materials could be used, including plastic. The upper portion 18 shown in FIG. 1 is configured to have an open toe and open back (heel), though other configurations are foreseeable including a closed back and/or closed toe construction. The upper portion 18 preferably has the open back construction seen in FIGS. 1 through 3 to provide greater size adjustability. This aspect of the invention is further promoted by the use of multiple straps 20, 22 and 24 to secure the shoe 10 to a casted foot 26. The shoe 10 is shown as having back, proximal and toe straps 20, 22 and 24, with each strap shown as being secured with a hook-and-loop closure 28, though other types of closures are possible and within the scope of this invention. The proximal strap 22 is preferably attached to the upper portion 18 with an elastic segment 30 to enable the wearer to better secure the cast shoe 10 to the wearer's cast by placing the strap (22) in elastic tension when fastening the strap 22 with the closure 28. The more secure closure provided by the elastic-containing proximal strap 22 is also believed to improve the gait of the wearer.

The outer sole 14 of the cast shoe 10 is relatively thick to better absorb impact. To further promote the absorption of impact, the material of the outer sole 14 is preferably a tough, soft, resilient and flexible material, and has a physical configuration as discussed in more detail below. A preferred material for the outer sole 14 is an air-insufflated thermoplastic resin. The construction and material of the outer sole 14 are chosen so that the entire sole 12 is flexible, including heel and toe portions 36 and 40 of the sole 12 where flexing occurs during the heel-strike and toe-off portions of gait.

As seen in FIG. 1, the outer sole 14 preferably has a curvature on its lower surface to provide a rocker bottom function in gait, with a rocker pivot line identified in FIG. 1 with reference number 34. The pivot line 34 is preferably located from the toe of the shoe 10 a distance of about one-third of the total length of the shoe 10. The flexibility of the sole 12 is believed to improve the rocker bottom gait. In the heel portion 36 and an intermediate portion 38 of the sole 12 located rearward of the pivot line 34, the outer sole 14 generally has a uniform thickness, preferably about three-quarters inch (about 2 cm). Forward of the pivot line 34, the toe portion 40 of the outer sole 14 tapers to decrease in thickness, preferably to about three-eighths inch (about 1 cm) at the toe of the shoe 10. As seen in FIG. 1, the last three-quarters inch (about 2 cm) or so of the heel portion 36 may be tapered or rounded to improve the gait of the wearer, more particularly the heel-strike portion of gait.

Figure 6:
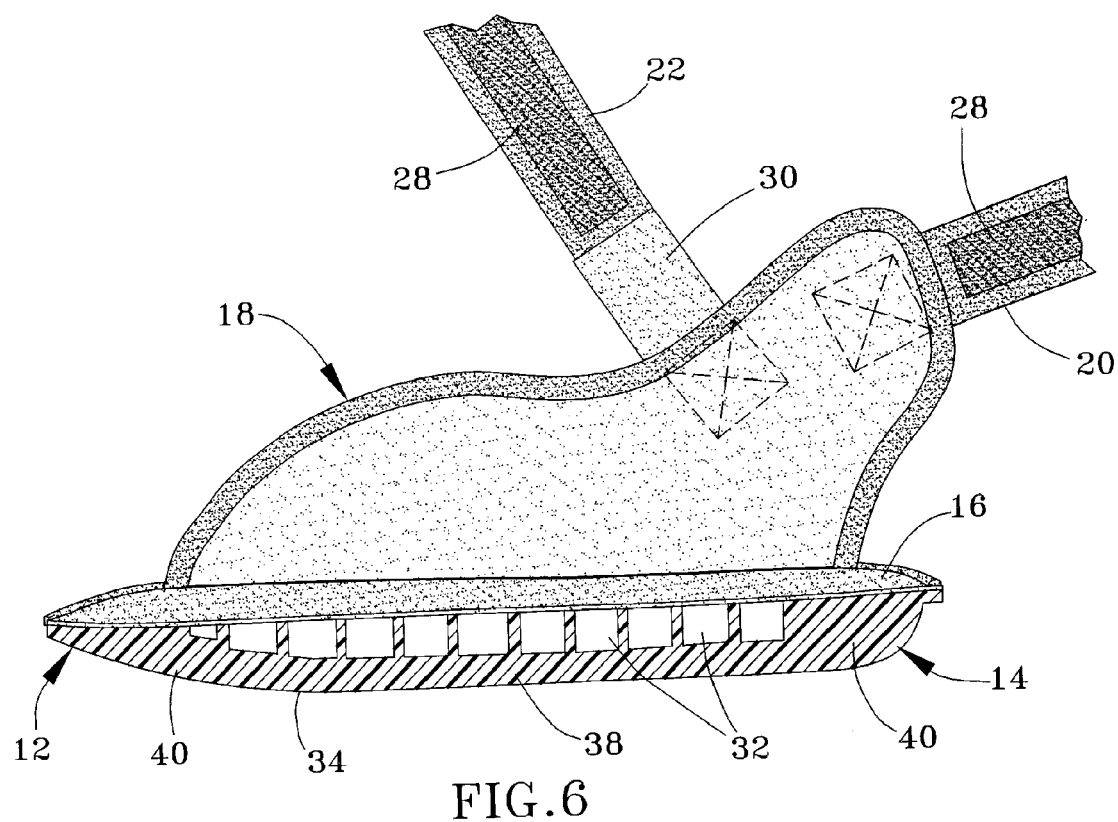
FIG. 6 is a cross-sectional view of the cast shoe.
Figure 7:
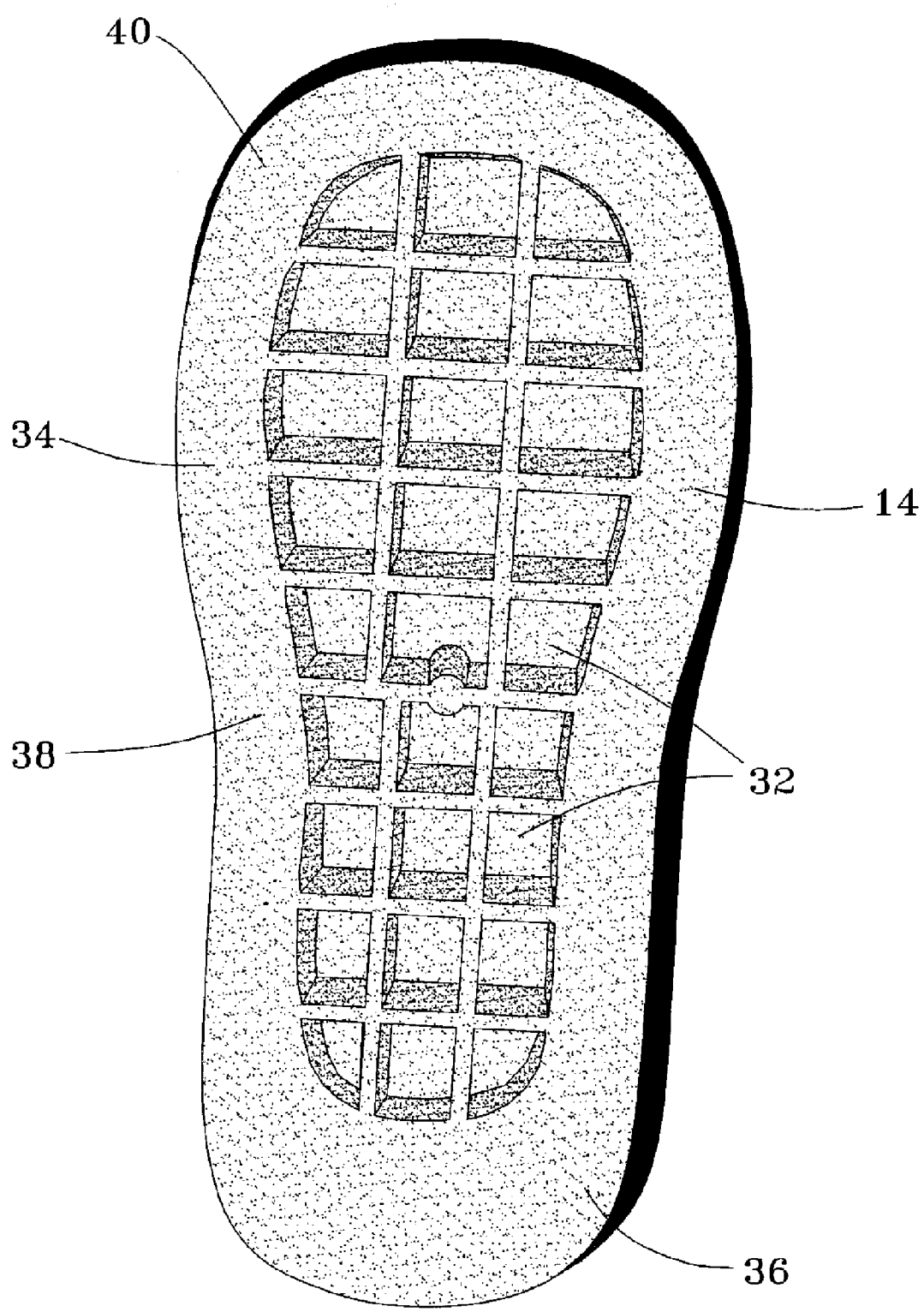
FIG. 7 shows the upper surface of the outer sole exposed by removal of the inner sole of the cast shoe of FIG. 1.

FIGS. 6 and 7 show, respectively, a cross-section of the shoe 10 and a plan view of the upper surface of the outer sole 14 as seen when exposed by removing the inner sole 16. The upper surface of the outer sole 14 is formed to have rows and columns of air pockets 32 that are normally closed by the inner sole 16 so that air is trapped within the pockets 32. The air pockets 32 have rectilinear shapes as a result of being delineated by a grid of flat walls that intersect each other at right angles. Because the walls that define the air pockets 32 are formed of the same resilient and flexible material as the remainder of the outer sole 14, the presence of the air pockets 32 greatly contributes to the flexibility of the sole 12, optionally to the extent that the shoe 10 can be bent over onto itself. From FIG. 7, it can be seen that the air pockets 32 located in the half of the outer sole 14 nearest the toe of the shoe 10 are larger than those located in the half of the outer sole 14 nearest the heel of the shoe 10. In the embodiment shown, the air pockets 32 generally have length dimensions in the toe-heel direction of the shoe 10 of about five-eighths inch (about 1.6 cm), while in the lateral direction those air pockets 32 nearest the heel have width dimensions of about one-half inch (about 1.3 cm) and those air pockets 32 nearest the toe have width dimensions of about eleven-sixteenths inch (about 1.7 cm). The depths of the pockets 32 within the heel and intermediate portions 36 and 38 of the outer sole 14 (i.e., rearward of the pivot line 34) are about one-half inch (about 1.2 cm), while the pockets 32 within the toe portion 40 of the outer sole 14 (i.e., forward of the pivot line 34) become progressively shallower as a result of the tapering of the toe portion 40 seen in FIG. 1.

Figure 3:
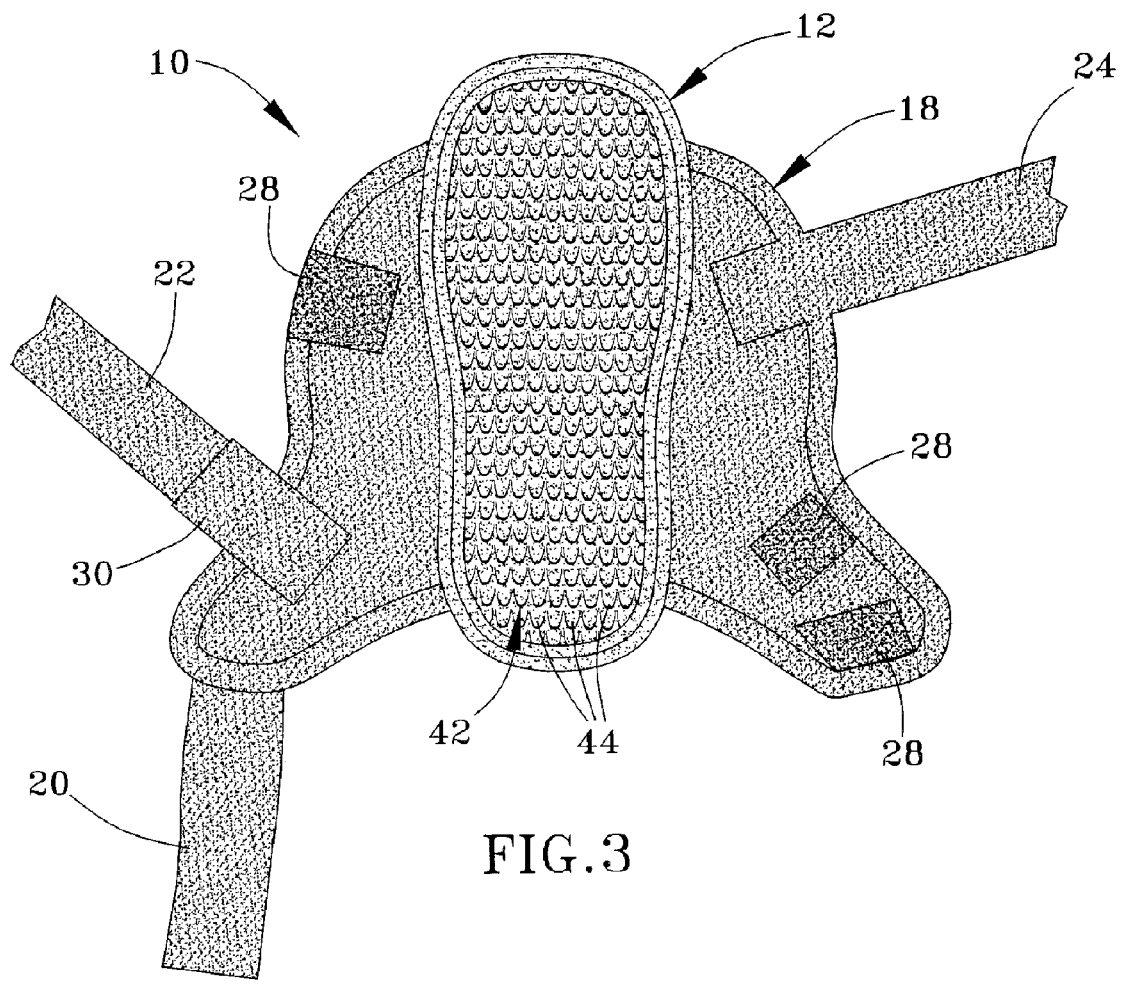
Figure 4:
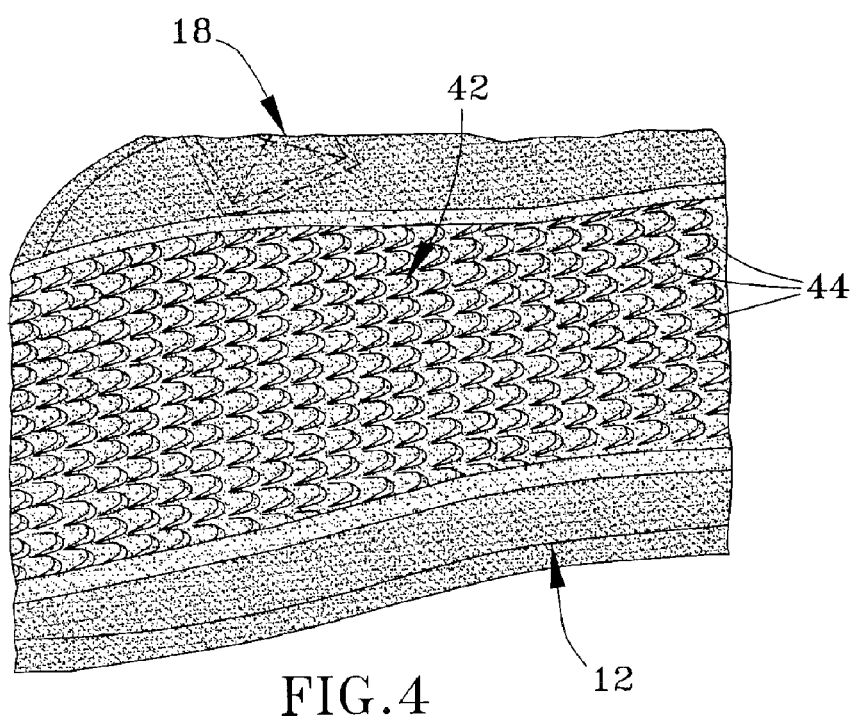
FIG. 4 shows in greater detail the sole of the cast shoe of FIG. 1.
Figure 5:
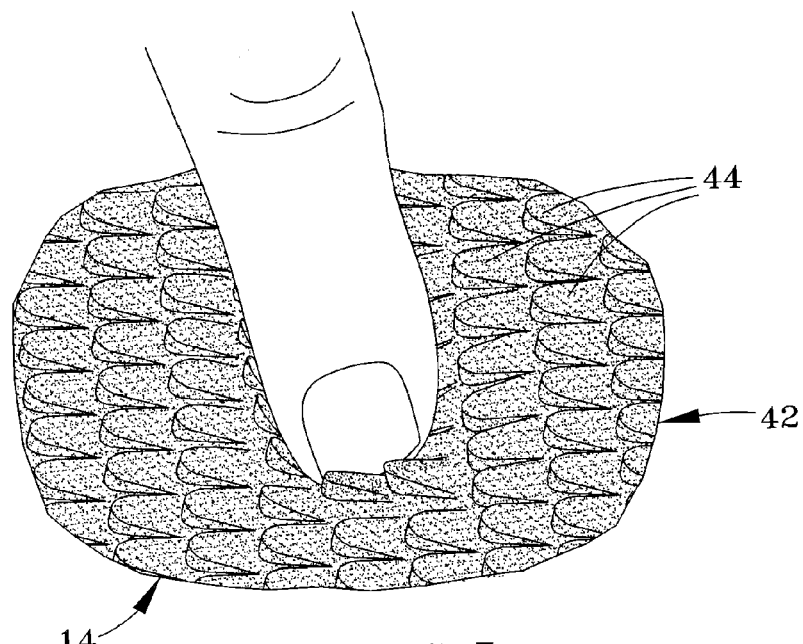
FIG. 5 is a perspective view of the sole evidencing the extreme resilience and flexibility of the sole in accordance with a preferred aspect of the invention.

From FIGS. 3, 4 and 5, the outer sole 14 can be seen to have a tread pattern 42 comprising individual raised tread elements 44. As most readily seen in FIG. 4, the elements 44 are arranged in rows and columns and generally D-shaped, with the curvature facing toward the heel of the shoe 10. Suitable dimensions for the elements are about one-quarter inch (about 0.6 cm) in both the toe-heel and lateral directions. Each tread element 44 is tapered to increase in thickness toward the heel of the shoe 10, generally to a maximum height of about one-sixteenth inch (about 0.2 cm). In contrast, the curved periphery of each element 44 is approximately perpendicular to the surface of the outer sole 14 from which the element 44 projects. The tapered shape of the elements 44 reduces the risk of snagging or catching the elements 44 on the surface being traveled by the wearer, while the abrupt peripheral edges of the elements 44 facing the heel of the shoe 10 provide traction on the push-off portion of gait.

The extreme resiliency and flexibility of the outer sole 14 are particularly evident from FIG. 5, which shows that the outer sole 14 can be resiliently indented from pressure applied by a single finger. Such flexibility in the sole 12 of a cast shoe 10 is unconventional in view of prior art practices and teachings that advocate the use of rigid soles for shoes intended to be worn on a casted foot.

In view of the above, the cast shoe 10 of this invention has several notable differences and advantages over the prior art. First, the cast shoe 10 has a thick outer sole 14 with curved characteristics, which combined with the soft, resilient thermoplastic resin construction gives a truer rocker bottom function in gait. In contrast to cast shoes of the prior art equipped with firm, rigid outer soles, the soft, resilient thermoplastic resin outer sole 14 of this invention is able to absorb considerably more impact force in the weight bearing stance phase of weight-bearing gait. As such, the cast shoe 10 diminishes patient discomfort and prolongs the function of the cast and the shoe 10 itself. The raised tread pattern 42 with sloping individual tread elements 44 reduces the risk of catching that would cause the patient to fall, while providing good traction on the push-off portion of gait. The elastic portion 30 of the proximal strap 22 enables the wearer to more firmly tighten the strap 22 and better hold the shoe 10 in place, thereby reducing the risk of catching while improving gait.

While the invention has been described in terms of a specific embodiment, it is apparent that other forms could be adopted by one skilled in the art. For example, the outer sole 14 could be modified to be formed of a thinner or thicker resilient thermoplastic resin material or formed of another material having similar flexibility and resilience, the tread pattern and tread element shape could be modified, the upper portion 18 could be modified to extend over the toes or around the back, any number of straps arranged differently from that shown in the Figures could be used, and additional elastic straps could be used, e.g., across the back and/or over the top of the shoe 10. It should also be understood that the phraseology and terminology employed above are for the purpose of disclosing the illustrated embodiment, and do not necessarily serve as limitations to the scope of the invention. The scope of the invention is to be limited only by the following claims.

What is claimed is:

1. A cast shoe for wearing on a casted foot, the cast shoe comprising:
    an outer sole formed of a resilient polymeric material to absorb impact, the outer sole having a heel portion of substantially uniform thickness, a tapered toe portion that is thinner than the heel portion, an upper surface, and a lower surface that is curved as a result of the tapered toe portion to provide a single rocker bottom function in gait;
    air pockets defined in the outer sole and containing entrapped air;
    an inner sole overlying and attached to the upper surface of the outer sole;
    a strap located adjacent the heel portion of the outer sole for securing the cast shoe to a casted foot; and
    a tread pattern on the lower surface of the outer sole;
    wherein the outer sole and the inner sole lack a rigid member and together the outer and inner sole define a sole that is flexible in its entirety.

2. The cast shoe according to claim 1, wherein the strap comprises an elastic portion to place the strap in tension when the cast shoe is on the casted foot and the strap holds the cast shoe to the casted foot.

3. The cast shoe according to claim 1, wherein the tread pattern comprises individual raised elements protruding from a surface of the outer sole.

4. The cast shoe according to claim 3, wherein each of the raised elements tapers to increase in thickness toward the heel portion.

5. The cast shoe according to claim 4, wherein each of the raised elements defines a peripheral wall that faces the heel portion and is approximately perpendicular to the surface of the outer sole.

6. The cast shoe according to claim 3, wherein each of the raised elements defines a peripheral wall that faces the heel portion and is approximately perpendicular to the surface of the outer sole.

7. The cast shoe according to claim 1, wherein the air pockets are defined in the upper surface of the outer sole and the inner sole closes at least some of the air pockets to entrap the air within.

8. The cast shoe according to claim 7, wherein the air pockets are arranged in rows and columns.

9. The cast shoe according to claim 8, wherein, the rows of the air pockets are oriented in a lateral direction of the cast shoe, and the columns of the air pockets are oriented in a toe-heel direction of the cast shoe.

10. The cast shoe according to claim 8, wherein at least some of the air pockets in the toe portion of the outer sole have larger volumes than at least some of the air pockets in the heel portion of the outer sole.

11. The cast shoe according to claim 1, further comprising an upper portion attached to the inner sole, the strap being attached to the upper portion.

12. A cast shoe for wearing on a casted foot, the cast shoe comprising:
   an outer sole formed of a resilient polymeric material to absorb impact, the outer sole having a heel portion of substantially uniform thickness, a tapered toe portion that is thinner than the heel portion, an intermediate portion between the heel and toe portions having a substantially uniform thickness that is substantially equal to the thickness of the heel portion, a rocker pivot line separating the toe and intermediate portions and located from and end of the toe portion a distance of about one-third of the total length of the cast shoe, an upper surface, and a lower surface that is curved as a result of the tapered toe portion to provide a single rocker bottom function in gait;
   air pockets defined in the upper surface of the outer sole;
   an inner sole overlying and attached to the upper surface of the outer sole so as to close the air pockets;
   an upper portion attached to the inner sole;
   a proximal strap attached to the upper portion adjacent the heel portion of the outer sole for securing the cast shoe to a casted foot; and
   a tread pattern on the lower surface of the outer sole, the tread pattern comprising individual raised elements protruding from a surface of the outer sole, each of the raised elements tapering to increase in thickness toward the heel portion;
   wherein the outer sole and the inner sole lack a rigid member and together the outer and inner sole define a sole that is flexible in its entirety.

13. The cast shoe according to claim 12, wherein the proximal strap comprises an elastic portion to place the proximal strap in tension when the cast shoe is on the casted foot and the proximal strap holds the cast shoe to the casted foot.

14. The cast shoe according to claim 12, wherein the raised elements are arranged in rows and columns on the lower surface of the outer sole, the rows of the raised elements are oriented in a lateral direction of the cast shoe, the columns of the raised elements are oriented in a toe-heel direction of the cast shoe.

15. The cast shoe according to claim 12, wherein the raised elements are D-shaped in plan view.

16. The cast shoe according to claim 15, wherein each of the raised elements defines a curved peripheral wall that faces the heel portion and is approximately perpendicular to the surface of the outer sole.

17. The cast shoe according to claim 12, wherein the air pockets are arranged in rows and columns.

18. The cast shoe according to claim 17, wherein the rows of the air pockets are oriented in a lateral direction of the cast shoe, and the columns of the air pockets are oriented in a toe-heel direction of the cast shoe.

19. The cast shoe according to claim 12, wherein at least some of the air pockets in the toe portion of the outer sole have larger volumes than at least some of the air pockets in the heel portion of the outer sole.

20. The cast shoe according to claim 12, wherein the inner sole closes at least some of the air pockets to entrap air within.

* * * * *